United States Patent
Tucker et al.

(10) Patent No.: US 10,183,031 B2
(45) Date of Patent: Jan. 22, 2019

(54) COMPOSITIONS CONTAINING VITAMIN D AND MAGNESIUM

(71) Applicants: Matthew Scott Tucker, Southlake, TX (US); Brett B. Bartel, Marietta, GA (US)

(72) Inventors: Matthew Scott Tucker, Southlake, TX (US); Brett B. Bartel, Marietta, GA (US)

( * ) Notice: Subject to any disclaimer, the term of this patent is extended or adjusted under 35 U.S.C. 154(b) by 0 days.

(21) Appl. No.: 15/050,417

(22) Filed: Feb. 22, 2016

(65) Prior Publication Data

US 2017/0239275 A1    Aug. 24, 2017

(51) Int. Cl.
*A61K 31/593* (2006.01)
*A61K 31/519* (2006.01)
*A61K 33/26* (2006.01)
*A61K 31/197* (2006.01)
*A61K 31/355* (2006.01)
*A61K 31/375* (2006.01)
*A61K 33/06* (2006.01)

(52) U.S. Cl.
CPC .......... *A61K 31/593* (2013.01); *A61K 31/197* (2013.01); *A61K 31/355* (2013.01); *A61K 31/375* (2013.01); *A61K 31/519* (2013.01); *A61K 33/06* (2013.01); *A61K 33/26* (2013.01)

(58) Field of Classification Search
CPC .. A61K 31/593; A61K 31/519; A61K 31/197; A61K 33/06; A61K 33/26
USPC ....................................................... 424/422
See application file for complete search history.

(56) References Cited

U.S. PATENT DOCUMENTS

| | | | | |
|---|---|---|---|---|
| 5,997,915 A | * | 12/1999 | Bailey | A23L 33/15 426/549 |
| 2011/0014277 A1 | * | 1/2011 | Bieley | A61K 31/07 424/450 |
| 2015/0305386 A1 | * | 10/2015 | Fernandez | A23L 33/15 426/2 |

FOREIGN PATENT DOCUMENTS

WO    WO2014209412    * 12/2014    ........... A23L 1/3045

OTHER PUBLICATIONS

Frank Lipman; title: Vitamin D: FAQ; The be well blogs; publish Sep. 24, 2009. Downloaded from https://www.bewell.com/blog/vitamin-d-faq//.*

* cited by examiner

*Primary Examiner* — Yanzhi Zhang
(74) *Attorney, Agent, or Firm* — Brett Bartel

(57) ABSTRACT

Described herein are manufactured compositions that contain vitamin D in an amount from 3500 IU to 5000 IU and magnesium in the form of magnesium L-5-methyltetrahydrofolate in an amount of about 1 mg. A manufactured composition contains vitamin D in an amount from 3500 IU to 5000 IU and magnesium in the form of magnesium L-5-methyltetrahydrofolate in an amount of about 1 mg and N-acetyl-L-cysteine magnesium chelate in the amount of 75 mg. A manufactured composition contains vitamin D in an amount from 3500 IU to 5000 IU and magnesium in the form of magnesium L-5-methyltetrahydrofolate in an amount of about 1 mg and N-acetyl-L-cysteine magnesium chelate in the amount of 75 mg, and iron.

13 Claims, No Drawings

COMPOSITIONS CONTAINING VITAMIN D AND MAGNESIUM

FIELD

The present disclosure generally relates to compositions comprising Vitamin D and Magnesium.

BACKGROUND

Vitamin D is a genus for a group of fat-soluble secosteroids responsible for enhancing intestinal absorption of minerals such as iron, magnesium, phosphate, calcium, and zinc. In humans, the most important compounds in this group are vitamin $D_2$ (ergocalciferol) and vitamin $D_3$ (also known as cholecalciferol). The synthesis of vitamin D in the skin is the main source of the vitamin. Dermal synthesis of vitamin D from cholesterol depends on sun exposure, specifically UVB radiation. Ergocalciferol and cholecalciferol can be ingested from diet and from supplements, since few foods contain vitamin D.

Magnesium is an important mineral that all cells in the human body need. Nearly half of the magnesium stored in the body is found in the body's organs and tissues, and the other half is found in our bones where it is found in combination with phosphorus and calcium. The body requires magnesium to carry out various biochemical functions such as enzyme activity. Magnesium deficiency can lead to a myriad of health conditions.

SUMMARY

A manufactured composition contains vitamin D in an amount from 3500 IU to 5000 IU and magnesium in the form of magnesium L-5-methyltetrahydrofolate in an amount of about 1 mg. A manufactured composition contains vitamin D in an amount from 3500 IU to 5000 IU, magnesium in the form of magnesium L-5-methyltetrahydrofolate in an amount of about 1 mg, and N-acetyl-L-cysteine magnesium chelate. A manufactured composition contains vitamin D in an amount from 3500 IU to 5000 IU, magnesium in the form of magnesium L-5-methyltetrahydrofolate in an amount of about 1 mg, N-acetyl-L-cysteine magnesium chelate, and iron.

DETAILED DESCRIPTION

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise.

"Optional" or "optionally" means that the subsequently described event or circumstance may or may not occur, and that the description includes instances where the event or circumstance occurs and instances where it does not.

As used herein, "subject" refers to a mammal, including a human that is in need of supplementation and/or benefits from the compositions and methods described herein.

As used herein, the term "rounded" means that an outer periphery of a structure is substantially free of angularity. For example, the outer periphery of microparticles can have spherical shapes and oval shapes that are free of angularity and have rounded shapes.

As used herein, the term "about" is used to provide flexibility to a numerical range endpoint by providing that a given value may be "slightly above" or "slightly below" the endpoint without affecting the desired result.

The disclosure provides various teachings on compositions containing vitamin D and magnesium. The ingredients, compounds, and chemicals that make up the elements of the compositions may contain vitamins, foods, or other organic matter that is prone to degradation after formulation in a finished product. It is common practice to formulate a nutritional finished product to include an "overage" or an additional amount of ingredient. Any amount of ingredient, compound, or chemicals that is within an "overage" of the ranges and amounts claimed and exemplified in this disclosure would be considered equivalent.

The disclosure provides compositions that contains vitamin D and magnesium and may be made up of different forms of magnesium in different salts and chelates in different ratios and amounts. Where the disclosure refers to an amount of an ingredient, it is measured by weight and not by molar amount. Where a total amount of an ingredient refers to a ratio between different forms or salts, it is measured by weight and not by molar amount. However, the specific form of chelate often refers to the ratio of metal and ligand in molar amounts. But, when the chelate is referenced as a component of a composition, then it typically refers to the weight of the chelate. In some aspects, only the mass or weight of the mineral comprising the chelate will be referenced, as in some aspects the value of the chelate is measured by the nutritional component of the mineral.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The nutritional compositions, dietary or compositions, and methods described herein can comprise, consist of, or consist essentially of the essential elements and limitations described herein, as well as any additional or optional ingredients, components, or limitations described herein or otherwise useful in nutritional formula applications.

The present nutritional compositions, compositions, and methods will now be described more fully hereinafter. However, these compositions and methods may be embodied in many different forms and should not be construed as limited to the representative embodiments set forth herein. The exemplary embodiments are provided so that this disclosure will be both thorough and complete, and will fully convey the scope of the disclosure and enable one of ordinary skill in the art to make, use, and practice the teachings of the present disclosure.

Nutritional Compositions

Described herein are nutritional compositions that include a body encapsulating magnesium and/or iron, a folate, and an additive, wherein the additive includes a microparticle having a core that includes Vitamin D and a coating. The body in the nutritional compositions described herein can include, but is not limited to, a tablet, an enteric coated tablet, a capsule, an enteric coated capsule, a softgel capsule, or an enteric coated softgel capsule encapsulating iron, folate, and the additives, for example the microparticles, described herein.

Microparticles

Microparticles can be included in the disclosed nutritional compositions, and more specifically, the microparticles described herein are preferably included within a tablet, an enteric coated tablet, a capsule, an enteric coated capsule, a softgel capsule, or an enteric coated softgel capsule.

The microparticles described herein generally include a microparticle core and a layer or a plurality of layers coated on an outermost surface of the microparticle core. The microparticle core is preferably made from a pharmaceutically acceptable material that includes, but is not limited to, tartaric acid, sugar, calcium carbonate, mannitol, microcrystalline cellulose, silica, starch or any combination thereof. These materials are mixed with the vitamin D and/or magnesium source.

It is preferable that the microparticle cores have a substantially rounded shape such that the microparticle cores do not aggregate during the production of the microparticles. In addition, because non-rounded shaped microparticle cores tend to aggregate and slow the production process, it is preferable that the microparticle cores have a rounded shape to facilitate production of rounded microparticles.

The microparticle cores described herein can be generally produced with any known extrusion and spheronization techniques that can obtain the desired microparticle diameters described below. For example, the microparticle core material can be subjected to radial extruding process, axial extruding process, cone extruding process, dome extruding process, die roller extruding process, or basket extruding process. These materials can be generally extruded through a die or mesh having variable sizes. For example, the die and mesh sizes associated with these extruding techniques can include 200 µm to 8000 µm, 300 µm to 7500 µm, 300 µm to 4000 µm, 300 µm to 2000 µm, 400 µm to 2000 µm, 400 µm to 1000 µm, and 500 µm to 800 µm to produce microparticle cores having a desired particle diameter. After extrusion, the microparticle core materials can be further subjected to any known spheronization treatment to further ensure sufficient microparticle core roundness.

In certain aspects, the microparticle cores can be further subjected to flow cytometry and separated based on desired microparticle core roundness. For example, in certain aspects, the desired microparticle core diameter ranges from 180 µm to 425 µm. In exemplary embodiments, the microparticles may have an accumulated volume average particle diameter D50 of from approximately 250 µm to approximately 425 µm to meet 40-60 mesh requirements. Or the microparticles may have an accumulated volume average particle diameter D70 of from approximately 180 µm to approximately 250 µm to meet 60-80 mesh requirements. Or the microparticles may have an accumulated volume average particle diameter D90 of from approximately 150 µm to approximately 180 µm to meet 80-100 mesh requirements.

In an exemplary embodiment, the microparticle cores may have a volume average particle size distribution index GSDv of approximately 1.30 or less. When GSDv is approximately 1.30 or less, little microparticle core aggregation occurs and sufficient microparticle roundness can be obtained.

The accumulated volume average particle diameter D50 and the average particle size distribution index of the microparticle cores may be measured, for example, in the following manner. Based on a particle size distribution measured with such a measuring device as Coulter Counter TA II (available from Beckman Coulter, Inc.) or Multisizer II (available from Beckman Coulter, Inc.), accumulated distributions of volume and number are each drawn from the small diameter side with respect to the divided particle size ranges. The particle diameters where the accumulated value is 16% are designated as volume D16V and number D16P, the particle diameters where the accumulated value is 50% are designated as volume D50V and number D50P, and the particle diameters where the accumulated value is 84% are designated as volume D84V and number D84P. By using these values, the volume average particle size distribution index (GSDv) is calculated as $(D84V/D16V)^{1/2}$, and the number average particle size distribution index (GSDp) is calculated as $(D84P/D16P)^{1/2}$. The microparticles may have a shape factor SF1 of from approximately 110 to approximately 140, and preferably from approximately 120 to approximately 140, which results in microparticle cores having little shape irregularity and having sufficient roundness (e.g., spherical shape).

SF1 is a shape factor that shows the extent of unevenness on the surface of the microparticle cores, and is calculated as follows. An optical micrograph of the microparticle cores scattered on a glass slide is acquired to a Luzex image analyzer through a video cam, and SF1 is calculated according to the following expression from the value obtained by dividing square of the maximum length of the toner particles by the projected area ((ML)2/A) for 50 toner particles, and the average value thereof is designated as SF1.

$$SF1=(ML)^2/a\times\pi/4\times100$$

wherein ML represents the maximum length of the toner particles, and A represents the projected area of the particles.

After obtaining microparticle cores having desirable roundness and diameter, the microparticle cores are then subjected to a coating process in which one or more coating layers are coated on an outermost surface of the microparticle cores. For example, in certain aspects, an outermost layer of the microparticle cores are coated with a solution, dispersion, or suspension. In some aspects, the coating may also contain additional magnesium or Vitamin D. In certain aspects, this coating can contain additional components that include, but are not limited to tocopherol and other preservatives, stabilizers, and excipients.

This coating can partially or completely coat the outermost layer of the microparticle core. In certain aspects, it is preferable that the coating completely coats the outermost layer of the microparticle core, and this combination of microparticle core and coating forms the microparticle. Depending on the type of material used for the microparticle core, it may be desirable to form an intermediary layer disposed between the outermost surface of the microparticle core. In one aspect the coating is pH dependent and may be used for targeting the absorption at specific locations in the GI tract. In this aspect, the intermediary layer may reduce or prevent the Vitamin D or magnesium from interacting and potentially blocking absorption.

In certain aspects, a plurality of coatings can be provided on the microparticle core in order to form the desired microparticle. In this aspect, the microparticle core can be coated with a coating containing Vitamin D or magnesium on the outermost surface of the microparticle core. In certain aspects, this coating is allowed to dry at a desired temperature and for a desired time period. Next, a second coating can be applied. In certain aspects, this second coating can include time release agents and additional excipients to more slowly and controllably administer, for example, the Vitamin D or magnesium to a subject. These time release coatings are described in greater detail further below. In further embodiments, additional coating layers can be provided on the microparticle cores.

In certain aspects, it is desirable that the microparticles do not exceed 500 μm in diameter because adverse effects such as gastrointestinal irritation may occur. It is also desirable that the microparticles have a substantially uniform shape and particle diameter to ensure efficient delivery to the subject. For example, in certain aspects, the microparticles described herein are monodisperse and have a polydispersity index (PDI) ranging from about 1.5 to 1, from about 1.3 to 1, and more preferably from about 1.2 to 1.

Vitamin D

Vitamin D is a genus of fat-soluble secosteroids responsible for enhancing intestinal absorption of iron, magnesium, phosphate, calcium, and zinc. In humans, the most important compounds in this group are vitamin $D_2$ (ergocalciferol) and vitamin $D_3$ (cholecalciferol). Ergocalciferol and cholecalciferol can be ingested from the diet and from supplements. Few foods contain vitamin D; synthesis of vitamin D (specifically cholecalciferol) in the skin is the major natural source of the vitamin. Dermal synthesis of vitamin D from cholesterol is dependent on sun exposure (specifically UVB radiation). Vitamin D from both the diet and dermal synthesis from sunlight is biologically inactive and requires activation through enzymatic conversion (hydroxylation) in the kidney and liver.

Vitamin D regulates calcium homeostasis by maintaining equilibrium (along with parathormone) between calcium resorption and excretion. If Vitamin D levels are low, then a person may lose significant calcium in the urine. If calcium intake is low, then poor bone mineralization is likely to occur in infants. Vitamin D may be provided through compositions of this disclosure in the form of vitamin $D_2$ (ergocalciferol) and/or vitamin $D_3$ (cholecalciferol).

Vitamin D is used for conditions of the heart and blood vessels, including high blood pressure and high cholesterol. It is also used for diabetes, obesity, muscle weakness, multiple sclerosis, rheumatoid arthritis, chronic obstructive pulmonary disease (COPD), asthma, bronchitis, premenstrual syndrome (PMS), and tooth and gum disease. Some people use vitamin D for skin conditions including vitiligo, scleroderma, psoriasis, actinic keratosis, and lupus vulgaris. Vitamin D in forms known as calcitriol or calcipotriene is applied directly to the skin for a particular type of psoriasis.

Vitamin D is a fat-soluble vitamin. Unlike water-soluble vitamins, fat-soluble vitamins dissolve in fat and are stored in body tissues. Because they are stored, over time they can accumulate to dangerous levels. Typically, high doses of Vitamin D are discouraged, except for persons with specific conditions who temporarily require high levels of Vitamin D.

In certain embodiments, the disclosed composition can optionally include pharmaceutically acceptable sources of Vitamin D in the range of from 500 IU to 8000 IU.

In certain aspects, the total amount of Vitamin D present in the composition is about 2500 IU. In certain aspects, the total amount of Vitamin D present in the composition is about 3775 IU. In certain aspects, the total amount of Vitamin D present in the composition is about 5000 IU. In certain aspects, the Vitamin D present in the composition is cholecalciferol.

In certain aspects, the total amount of Vitamin D thereof present in the composition ranges from 100 IU to 6000 IU, 100 IU to 5000 IU, 100 IU to 4000 IU, 100 IU to 3000 IU, 100 IU to 2000 IU, 100 IU to 10000 IU, 500 IU to 5000 IU, 500 IU to 4000 IU, 500 IU to 3000 IU, 500 IU to 2000 IU, 500 IU to 1000 IU, 1000 IU to 5000 IU, 1000 IU to 4500 IU, 1000 IU to 4000 IU, 1000 IU to 3500 IU, 1000 IU to 3000 IU, 1000 IU to 2500 IU, 1000 IU to 2000 IU, 1000 IU to 1500 IU, 2000 IU to 4000 IU, 2000 IU to 3500 IU, 2000 IU to 3000 IU, 2000 IU to 2500 IU, 3000 IU to 5000 IU, 3000 IU to 4500 IU, 3000 IU to 4000 IU, 3000 IU to 3500 IU, or any range having endpoints falling within any of the preceding ranges.

In certain aspects, Vitamin D is not included in the microparticles of the nutritional composition. In other aspects, a portion of Vitamin D is included in any of the coated layers of the microparticles and another portion of Vitamin D is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of Vitamin D is not in the microparticles, and in this aspect, the remainder of Vitamin D can be included in the microparticle.

In certain aspects Vitamin D is provided in a composition without microparticles as described above.

Magnesium

Magnesium is an important mineral that is needed by every cell in the human body.

About half of the magnesium stores in the body are found in the cells of the body's organs and tissues, and the other half is found in bones where it is found in combination with phosphorus and calcium. The human body requires magnesium to carry out various biochemical functions including various enzyme activities. Magnesium deficiency can lead to a myriad of health conditions.

Magnesium is a vital nutrient that is often deficient in modern diets. Our ancient ancestors would have had a ready supply from organ meats, seafood, mineral water, and even swimming in the ocean, but many modern soils are depleted of minerals, and magnesium is removed from water during routine municipal treatment. The current RDA for adults is between 320 and 420 mg daily, and the average US intake is around 250 mg daily.

Magnesium plays an important role in biochemical reactions all over the body. It is involved in a lot of cell transport activities, in addition to helping cells make energy aerobically or anaerobically. Bones are a major reservoir for magnesium, and magnesium is the counter-ion for calcium and potassium in muscle cells, including the heart. If the body's magnesium is too low, it can experience muscle cramps, arrhythmias, and even sudden death. Ion regulation is important with respect to how muscles contract and nerves send signals. In the brain, potassium and sodium balance each other. In the heart and other muscles, magnesium pulls some of the load.

Magnesium also is designed to offset calcium. Magnesium is very important to bone health and balances out calcium to ensure a working body. Without magnesium, calcium can actually become toxic and affect brain health.

Magnesium may be used to improve anxiety, apathy, depression, headaches, insecurity, irritability, restlessness, talkativeness, and sulkiness. Magnesium deficiency has been reported to cause depression, behavioral disturbances, headaches, muscle cramps, seizures, ataxia, psychosis, and irritability. Magnesium supplementation can improve all of these conditions. Some forms of magnesium can be more effective. Additionally, the combination of magnesium with other nutrients can have a synergistic effect on improving these conditions. The combination of high doses of Vitamin D and magnesium supplementation improves magnesium absorption and utility. Additionally, magnesium may be provided as a salt or chelate to an additional nutrient. This way one ingredient may provide a synergistic affect that neither nutrient could provide alone.

Inadequate dietary intake of magnesium also may lead to different health conditions, including: loss of appetite, disorientation, confusion, psychotic behavior, depression, tremors, convulsions, numbness, tingling, and cramps in the muscles, vasodilation, or widening of the blood vessels, coronary spasms, abnormal heart rhythms, seizures, osteoporosis, cerebral infarction, irritability of the nervous system.

Stress also affect magnesium stores. During periods of extreme stress, magnesium is often used up by the body. This causes a compounding affect since people who are magnesium deficient, are prone to anxiety; and then these people use up their magnesium reserves as a result of their anxiety, which contributes to more anxiety and more stress.

Magnesium may be depleted excessively through the urine and gastrointestinal that leads to malabsorption of magnesium or excessive loss of magnesium in the stool resulting in magnesium deficiency.

Magnesium deficiency is likely common in the United States. Some studies have shown that the diets of most of the adult population in America are deficient in magnesium, and it was also found that compared to Hispanics or non-Hispanic whites, the non-Hispanic black population consumed lower amounts of magnesium, and that people who were 70 years of age and above consumed less magnesium compared to younger adults.

Treatments that involve diuretics, certain medications used for treating cancer, and certain antibiotics, can lead to an increase of the loss of magnesium through urine. Diabetes that is not adequately controlled can result in magnesium being lost excessively in urine, resulting in depleted magnesium stores in the body. Alcohol also leads to magnesium being excreted excessively in the urine, and a high intake of alcohol has been linked to magnesium deficiency. Excessive or chronic diarrhea and vomiting can also lead to deficiency due to the depletion of the mineral. Some of the other possible causes of magnesium depletion in the body are: postoperative complications subsequent to bowel resection, parenteral fluids being administered without adding magnesium salts, and nasogastric suctioning; and malnutrition or starvation.

Loss of magnesium in excessive amounts can be the result of: diabetic acidosis and severe dehydration; hypoparathyroidism and hyperaldosteronism, resulting in hypocalcemia and hypokalemia; hypercalcemia and hyperthyroidism; adrenocortical hormones being released in excessive amounts. Magnesium deficiency can also be primarily due to genetic disorders.

The Recommended Dietary Allowance, or RDA for males is: 410 mg for ages 14 to 18; 400 mg for ages 19 to 30; 420 mg for ages 31 and above. The RDA for females is: 360 mg for ages 14 to 18; 310 mg for ages 19 to 30; 320 mg for ages 31 and above. During pregnancy the RDA is increased to 400 mg (for 14 to 18 years of age). For pregnant women aged 19 to 30, the RDA is 350 and for age above 31 years, it is 360.

Magnesium deficiency can be treated. If there is only a mild deficiency of magnesium, it can be restored to healthy levels by increasing the intake of magnesium in the diet. Adults at risk of magnesium deficiency can get their recommended amounts by consuming dark green leafy vegetables as well as at least five servings of vegetables and fruits every day. Rice, wheat bran, and oats are some of the grains that are high in magnesium.

Magnesium supplements may provide adequate nutrition, but some forms, especially magnesium salts, can lead to diarrhea. Many commercial nutritional supplements contain magnesium oxide, which is a form of magnesium that is absorbed the least efficiently by the human body.

Compositions providing magnesium to patients are also used to supplement a person's magnesium deficiency. Magnesium may be provided through many different pharmaceutically acceptable salts or chelates and one skilled in the art would know of these salts and chelates. The magnesium may be provided by one of many magnesium sources such as magnesium citrate, magnesium sulfate, magnesium oxide, magnesium chloride, magnesium acetate, magnesium hydroxide, magnesium gluconate, magnesium fumarate, magnesium lactate, and combinations thereof, though other sources may be used as known by those skilled in the art.

Chelated magnesium can provide better absorption than many magnesium salts currently used. This is because chelated minerals are better absorbed and readily disassociate. Many amino acids are known to form chelates with magnesium and enhance bioavailability. When minerals such as magnesium are chelated, they are more likely to survive the passage from the stomach to the small intestines intact. Accordingly, more chelated magnesium will be absorbed in the intestinal tract than magnesium that is non-chelated.

Patients with HIV are known to have decreased glutathione and cysteine levels, and they are also known to have magnesium deficiency. Since N-Acetyl-L-Cysteine is the precursor to glutathione, an NAC-magnesium chelate is synergistically beneficial for an HIV patient.

Additionally, magnesium is an obligatory cofactor in glutathione synthesis. As a result, magnesium deficiency may impair glutathione synthesis. In addition, many neurodegenerative conditions have been reported to be associated with decreased brain magnesium levels and increased oxidative stress. A composition providing a source of NAC-magnesium chelate can increase both brain magnesium and glutathione levels. Additionally, because NAC crosses the blood brain barrier, it would be an effective treatment for neurodegenerative conditions.

The source of magnesium used for chelation with NAC may be one of many magnesium sources such as magnesium sulfate, magnesium oxide, magnesium chloride, magnesium acetate, magnesium hydroxide, magnesium gluconate, magnesium fumarate, magnesium lactate, and combinations thereof, though other sources may be used as known by those skilled in the art.

In the disclosed nutritional composition, it is preferable to include magnesium in the total amount of about 0.1 mg/kg to 6 mg/kg, 2.5 mg/kg to 5.5 mg/kg, 3 mg/kg to 5 mg/kg, 3.5 mg/kg to 4.5 mg/kg, or any range having endpoints falling within any of the preceding ranges of a subject's body mass. For example, if the subject has a body mass of 100 kg (i.e., 220 lbs), it is preferable to orally administer 5 mg to 600 mg of magnesium to this subject when using the 2 mg/kg to 6 mg/kg range. Total amounts of magnesium in the composition falling below 1 mg/kg are potentially inadequate to prevent or reduce problems associated with magnesium deficiency. Furthermore, total amounts of magnesium exceeding 6 mg/kg may be associated with unwanted side effects associated such as magnesium poisoning if administered for an extended period of time. Therefore, in certain aspects, the total amount of magnesium thereof present in the composition ranges from 1 mg to 600 mg, 10 mg to 500 mg, 10 mg to 400 mg, 10 mg to 300 mg, 10 mg to 200 mg, 10 mg to 100 mg, 50 mg to 500 mg, 50 mg to 400 mg, 50 mg to 300 mg, 50 mg to 200 mg, 50 mg to 100 mg, 100 mg to 500 mg, 100 mg to 450 mg, 100 mg to 400 mg, 100 mg to 350 mg, 100 mg to 300 mg, 100 mg to 250 mg, 100 mg to 200 mg, 100 mg to 150 mg, 200 mg to 400 mg, 200 mg to 350 mg, 200 mg to 300 mg, 200 mg to 250 mg, 300 mg to 500 mg, 300 mg to 450 mg, 300 mg to 400 mg, 300 mg to 350 mg, or any range having endpoints falling within any of the preceding ranges.

In certain aspects, the total amount of magnesium present in the composition is about 5 mg. In certain aspects, the total amount of magnesium present in the composition ranges from 0.5 mg to 100 mg based on the total weight of the composition.

In certain aspects, magnesium is not included in the microparticles of the composition. In other aspects, a portion of magnesium is included in any of the coated layers of the microparticles and another portion of magnesium is included in the encapsulating body (e.g., tablets and capsules) that is not the microparticle. For example, in certain aspects, at least 90%, 85%, 80%, 75%, 70%, 65%, 60%, 55%, or 50% of the overall amount of magnesium is not in the microparticles, and in this aspect, the remainder of the magnesium can be included the microparticle.

Folate

A pharmaceutically acceptable form of folic acid, folic acid derivatives, folate, reduced folate, or any combination thereof is included within the composition. Folate has been shown to play a broad role in nucleotide synthesis, catecholamine (Dopamine, Norepinephrine, and Serotonin) synthesis, and methylation in mammals. Moreover, folic acid is known to play a role in nucleotide biosynthesis processes, and more specifically in the synthesis of thymine from uracil (i.e., dUMP, deoxyuracil monophosphate). In adult humans, folic acid supplementation has been implicated in reducing megaloblastic anaemia often associated with folate deficiency and/or side effects associated with various medical treatments (e.g., chemotherapy). Women during periconceptual periods, people with alcoholism, irritable bowel syndrome, celiac disease, and depression may benefit from supplements to natural folate due to its critical role in neural development, catecholamine regulation, gene expression, cell division, and blood cell formation.

In addition to its role in biosynthesis, folate is important in trans-methylation, which is of broad relevance for human health. Trans-methylation is the process by which DNA, RNA, proteins, lipids, and neurotransmitters are methylated (acquire a methyl group through alkylation) This methyl group assignment regulates the function of for instance genes, (i.e. epigenetics), and myelin basic protein; interruptions in the methylation cycle or deviant distribution of the methyl groups can play an essential role in development of cancer and neuropathy (including paralysis).

Two folate species reduced from folic acid, dihydrofolate and tetrahydrofolate, are not directly involved in the metabolic pathway, but instead transfer one-carbon moieties toward either methylation or DNA synthesis pathways. Methotrexate (a common chemotherapy drug) is a competitive and irreversible inhibitor of the rate limiting enzyme dihydrofolate reductase that converts folic acid to its reduced forms, thereby tightly regulating the folate cycle via feedback and end product inhibition.

One form of reduced folic acid, folinic acid, is incorporated into purine (used by the mammalian body in DNA and RNA synthesis and repair) during biosynthesis. Two of the four bases of DNA, two of the four building blocks of RNA, and a significant component in a suite of important biomolecules are purines. In some aspects, folinic acid may be provided as a calcium salt or a magnesium salt.

The bioavailable form of folate, L-5-methyltetrahydrofolate, 5-methyltetrahydrofolate, or L-methylfolate is essential for the synthesis and protection of tetrahydrobiopterin, a rate limiting cofactor in the production of melatonin and central catecholamines: Dopamine, Norepinephrine, and Serotonin. Since magnesium also plays a role in the production of these important neurotransmitters, a composition that provides magnesium in the form of magnesium L-5-methyltetrahydrofolate has a synergistic affect.

It is also a cofactor in the production of nitric oxide, important in the regulation of blood pressure and blood flow. Endothelial nitric oxide is dependent on tetrahydrobiopterin availability and affects the disease state in individuals with diabetes, artherosclerosis, and hypoxic pulmonary hypertension. Additionally, L-methylfolate also regulates homocysteine metabolism, increased plasma levels of which are a risk factor for vascular disease and pregnancy complications. For these reasons and others, L-methylfolate may be an important supplement in the maintenance and treatment of both mental and vascular health.

In addition, folic acid supplementation has been shown to play a role in preventing neural tube defects that occur during pregnancy. For example, although the molecular and physiological mechanisms are currently unknown, folic acid supplementation has been theorized to reduce the occurrence of spina bifida by up to 70%. Thus, for at least these reasons, it is desirable to include a pharmaceutically acceptable form of folic acid and folic acid derivatives in the disclosed compositions.

Various forms of folate are present in the human diet. Leafy green vegetables have high concentrations, and some folate may be found in eggs.

In certain aspects, folate derivatives having substituents at its $N^5$ or $N^{10}$ position have increased stability and are less prone to cleavage and oxidation. Thus, these folic acid derivatives may be favored in the disclosed compositions. For example, in certain aspects, it is preferable that at least one of folic acid, 10-formyl folic acid, 5-formyl tetrahydrofolate, 5-methyl tetrahydrofolate, or any combination thereof is present at a higher concentration in the nutritional composition than dihydrofolate and tetrahydrofolate, and in certain aspects, dihydrofolate and/or tetrahydrofolate are not present in the composition.

Folic acid also has shown to have limitations when provided at dosages near 1 mg or more as the enzyme dihydrofolate reductase is not an efficient enzyme and has been shown to saturate at high levels. This causes the concentration of unmetabolized folic acid in the blood to increase and has been known to have complications. Additionally, some people with specific genotypes have problems with the MTHFR enzyme and cannot effectively reduce folic acid to the biologically active form of folate: L-Methylfolate. Compositions supplementing folate having reduced forms of folate can be preferred. Additionally, some compositions may provide multiple forms of folate to ensure a patient is able to absorb the folate.

The total biologically active amount of folate: folic acid and derivatives thereof present in the composition ranges from 100 μg to 15 mg. Total biologically active amounts of folic acid and derivatives thereof below 100 μg are potentially inadequate to prevent or reduce problems associated with folate deficiencies (e.g., megaloblastic anaemia, neural tube defects in fetuses, etc.). Pregnant mothers are recommended to take between 400 mcg and 1 mg of folate. High dosages of folate have been shown to improve a number of human ailments and conditions including impaired cognitive function, ADHD, memory loss, diabetic peripheral neuropathy, and depression. Therefore, in certain aspects, the total biologically active amount of folate and derivatives thereof present in the composition from 100 μg to 15 mg, 400 μg to 800μg, 400 μg to 1000μg, 800 μg to 1000μg, 1 mg to 3 mg, 3 mg to 6 mg, 7.5 mg to 15 mg, or any range having endpoints falling within any of the preceding ranges. These amounts may reflect the total amount of folate moiety or the amount of the folate compound including the salt.

In certain aspects, the total amount of folate, folic acid, and reduced folate derivatives present in the nutritional composition ranges from 0.1 mg to 20 mg based on the total weight of the nutritional composition.

The term "total folate" typically refers to the combined amount of folate compounds.

This typically includes accounting for the salt, even though the folate moiety is less. Reference to total folate should account for the entire compound unless stated otherwise.

Folate may be provided through many different pharmaceutically acceptable salts. For example, L-methylfolate may be in a salt with calcium, magnesium, zinc, or any other ion known in the art. 5-formyl tetrahydrofolate may also be administered in any pharmaceutically acceptable salt. In one aspect, the folate may be provided in the form of a magnesium L-5-methyltetrahydrofolate salt.

An important factor for proper absorption of minerals involves the way the minerals interact with each other. Calcium, for example, might deplete stores of vitamin D and magnesium as it enters the bloodstream. Metafolin® is a commercial form of L-methylfolate calcium and has a large percentage of the commercial market. As L-methylfolate calcium is the predominate form of commercial L-methylfolate calcium, other forms have not been available to manufacturers of nutritional compositions. While calcium-folate salts are well known in the industry, in certain applications, a different salt would be preferred. A magnesium L-5-methyltetrahydrofolate salt might be preferable to an L-methylfolate calcium salt where magnesium and vitamin D absorption is a concern. The combination of the magnesium moiety and folate moiety have a synergistic affect. And magnesium L-5-methyltetrahydrofolate, or levomefolate magnesium, is actually more soluble than L-methylfolate calcium. In one aspect, the composition comprises 1 mg of levomefolate magnesium.

In certain aspects, the folic acid and folate derivatives are not included in the microparticles of the nutritional composition. In other aspects, a portion of the folic acid and folate derivatives are included in any of the coated layers of the microparticles and another portion of the folic acid and folate derivatives are included in the encapsulating body (e.g., tablets and capsules) that is not the microparticle. For example, in certain aspects, at least 90%, 85%, 80%, 75%, 70%, 65%, 60%, 55%, or 50% of the overall amount of the folic acid and folic acid derivatives are not in the microparticles, and in this aspect, the remainder of the folic acid and folic acid derivatives can be included in the microparticle.

Iron

A pharmaceutically acceptable form of iron is also included within the disclosure and may be provided through many different pharmaceutically acceptable salts. In the human body, iron is a key component, which is often complexed with various porphyrin rings to facilitate numerous metabolic and biological processes. More specifically, iron is often complexed with heme groups to form hemoglobin, and iron is also often complexed with various cytochromes (e.g., Cytochrome C in the mitochondria) to carry out electron transport during the production of adenosine tri-phosphate (i.e., ATP) in the mitochondria.

In humans, iron deficiency is usually associated with various anemias, thrombocytosis, decreased immunity, increased susceptibility to sepsis, increased maternal mortality, and atrophy of mucous membranes (e.g., Plummer-Vinson syndrome). Furthermore, iron deficiency in pregnant mothers, can potentially lead to low birth weights, preterm birth, and under development in a newborn child. Thus, for at least these reasons, it is desirable to include a pharmaceutically acceptable form of iron in the disclosed nutritional compositions.

Iron supplementation has a number of challenges. Ferric iron is very slow to absorb, can cause constipation, but does have milder side effects than Ferrous iron supplements. Ferrous iron supplements are more readily dissolved and absorbed, however, they are also accompanied by side effects such as nausea, cramps, and metal tasting. Other forms of iron include heme iron, polysaccharide iron complexes, and chelated iron.

Since iron absorption can be problematic, in some aspects it is beneficial to provide iron through multiple forms of iron to encourage better absorption. This also has the ability to reduce side effects.

Iron is absorbed as either a heme iron or nonheme iron. A heme iron has an intact metalloporphyrin ring. A nonheme iron is an ionic iron. Heme iron is principally found in meat as hemoglobin or myoglobin and is more readily and effectively absorbed than nonheme iron. This provides a significantly greater dietary source of iron than nonheme iron.

In one aspect, the composition provides chelated iron(s) in combination with heme iron and/or heme iron polypeptide, wherein heme iron polypeptide is preferably in the form of a proteolytic digest of bovine and/or porcine hemoglobin; however, it should be recognized that other derivations of heme iron polypeptide may be procured from the hemoglobin and/or myoglobin molecular complexes of alternate animal species. In one aspect the composition provides between 3 and 10 mg of heme iron. In one aspect, 6 mg of heme iron is provided in the composition.

The iron supplemented through polysaccharide-iron complex have greater bioavailability and fewer side effects. In one aspect the composition provides between 15 and 30 mg of iron through polysaccharide complexes. In one aspect, 21 mg of iron is provided in a polysaccharide complex.

In one aspect the composition provides between 5 and 70 mg of chelated iron. In one aspect, 9 mg of iron is provided in a polysaccharide complex.

While less preferred, iron may be provided through many different pharmaceutically acceptable salts and one skilled in the art would know of these salts and chelates. Some pharmaceutically acceptable forms of iron supplementation may be through carbonyl, ferrous gluconate, ferrous fumerate, iron amino acid complexes, ferronyl carbonate, iron chelates, among others not listed.

In certain aspects, the total amount of iron present in the composition is about 27.5 mg. In certain aspects, the total amount of iron present in the composition ranges from 0.5 mg to 100 mg based on the total weight of the composition.

In some aspects of the disclosed nutritional composition, it is preferable to include iron in the total amount of about 0.1 mg/kg to 6 mg/kg, 2.5 mg/kg to 5.5 mg/kg, 3 mg/kg to 5 mg/kg, 3.5 mg/kg to 4.5 mg/kg, or any range having endpoints falling within any of the preceding ranges of a subject's body mass. For example, if the subject has a body mass of 100 kg (i.e., 220 lbs), it is preferable to orally administer 1 mg to 300 mg of iron to this subject when using the 2 mg/kg to 6 mg/kg range. Total amounts of iron in the composition falling below 1 mg/kg are potentially inadequate to prevent or reduce problems associated with iron deficiency. Furthermore, total amounts of iron exceeding 6 mg/kg may be associated with unwanted side effects associated such as iron poisoning if administered for an extended period of time. Therefore, in certain aspects, the total amount of iron thereof present in the composition ranges from 1 mg to 300 mg, 5 mg to 300 mg, 5 mg to 200 mg, 5 mg to 150 mg, 5 mg to 100 mg, 6 mg to 54 mg, 12 mg to 36 mg, 18 mg to 27 mg, or any range having endpoints falling within any of the preceding ranges.

In certain aspects, iron is not included in the microparticles of the composition. In other aspects, a portion of iron is included in any of the coated layers of the microparticles and another portion of iron is included in the encapsulating body (e.g., tablets and capsules) that is not the microparticle. For example, in certain aspects, at least 90%, 85%, 80%, 75%, 70%, 65%, 60%, 55%, or 50% of the overall amount of iron is not in the microparticles, and in this aspect, the remainder of the iron can be included the microparticle.

N-Acetyl-L-Cysteine

N-acetyl-L-cysteine is the acetylated precursor of the amino acid L-cysteine and is also known as N-acetyl cysteine, N-acetyl-L-cysteine or NAC. NAC is a derivative of cysteine with an acetyl group attached to its nitrogen atom and like most thiols (RSH) can be oxidized by a large variety of radicals and also serve as a nucleophile (electron pair donor). NAC is a metal binding compound, as is the case with other thiols, having two potential coordination sites at the thiol and carboxyl groups where the latter is deprotonated at neutral pH. NAC is capable of binding transition metal ions, such as Mg(II), Zn (II), and Fe(III), and heavy metal ions such as Cd(II), Hg(II), and Pb(II) primarily through its thiol side chain and others.

NAC has been shown to exert survival-promoting effects in several cell systems. Cysteine is transported mainly by the alanine-serine-cysteine (ASC) system, a ubiquitous system of Na+-dependent neutral amino acid transport, in a variety of cells. NAC is a membrane-permeable cysteine precursor that does not require active transport and delivers cysteine to the cell in a unique way.

After free NAC enters a cell, it is rapidly hydrolyzed to release cysteine, a precursor of glutathione (GSH). GSH is synthesized intracellularly by the consecutive actions of c-glutamylcysteine synthetase and GSH synthetase. The synthesis of GSH is limited by the availability of substrates; cysteine is usually the limiting precursor. c-Glutamylcysteine synthetase is inhibited by feedback from GSH (Ki about 1.5 mM). Thus, under physiological conditions, this enzyme is probably not operating at its maximal rate. In addition, intracellular GSH is maintained in its thiol form by glutathione reductase, which requires NADPH. GSH participates nonenzymatically and enzymatically (GSH S-transferases (GSTs)) in protection against toxic compounds. Perhaps one of its most important functions is protection against oxidative damage caused by reactive oxygen species (ROS), many of which are generated during normal metabolism. In addition, GSH can react nonenzymatically with ROS and GSH peroxidase (and non-selenium (Se) peroxidase) to catalyze the destruction of hydrogen peroxide and hydroperoxides. Thus, NAC is an antioxidant and a free radical scavenging agent that increases intracellular GSH, a major component of the pathways by which cells are protected from oxidative stress.

NAC has been shown to interact with various metabolic pathways including, but not limited to, regulation of cell cycle and apoptosis; carcinogenesis and tumor progression; mutagenesis; gene expression and signal transduction; immune-modulation; cytoskeleton and trafficking; and mitochondrial functions.

Oxidative stress has been shown to play a pivotal role in neuronal dysfunction and death in various neurodegenerative diseases, including sickle cell disease (SCD), myoclonus epilepsy of the Unverricht-Lundborg type, Alzheimer's disease, Parkinson's disease, tardive dyskinesia, and Down's syndrome. Free radical damage from oxidative stress has long been thought to play an important role in age-related neurodegenerative disorders. It has been suggested that free radical damage compromises composition integrity of cell membranes, which decreases membrane fluidity.

Oxidative stress can in some cases result in cognitive impairments. Antioxidants have been found to both prevent, treat, and reverse learning and memory deficits induced by free radicals. NAC is an antioxidant used to combat oxidative stress-induced damage. Studies have shown that NAC protects against oxidative stress in peripheral tissues and in the central nervous system. Additionally, it has been found to reverse age-related impairments in memory.

In certain embodiments, the disclosed composition can optionally include pharmaceutically acceptable N-Acetyl-L-Cysteine in the range of from 25 mg to 1000 mg, 50 mg to 900 mg, 100 mg to 800 mg, 100 mg to 700 mg, 100 mg to 600 mg, 100 mg to 500 mg, 100 mg to 400 mg, 100 mg to 300 mg, 100 mg to 200 mg, 200 mg to 800 mg, 200 mg to 650 mg, 200 mg to 500 mg, 200 mg to 450 mg, 200 mg to 300 mg, 300 mg to 750 mg, 300 mg to 600 mg, 300 mg to 500 mg, 300 mg to 450 mg, 300 mg to 400 mg, 400 mg to 650 mg, 400 mg to 600 mg, 400 mg to 550 mg, 400 mg to 500 mg, 400 mg to 450 mg, or any range having endpoints falling within any of the preceding ranges.

In certain aspects, the total amount of NAC present in the composition ranges from 50 mg-1000 g based on the total weight of the composition. In one aspect, the total amount of NAC present in the composition is 70 mg based on the total weight of the composition.

In certain aspects, NAC is not included in the microparticles of the nutritional composition. In other aspects, a portion of NAC is included in any of the coated layers of the microparticles and another portion of NAC is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of NAC is not in the microparticles, and in this aspect, the remainder of NAC can be included in the microparticle.

In one aspect, the composition contains about 75 mg of NAC:Mg. This provides about 5.2 mg of magnesium and 70 mg of NAC.

In one aspect, the composition contains about 64 mg of NAC:Fe (1:2). This provides about 9 mg of iron and 55 mg of NAC. NAC:Fe can also be in the ratio of 1:3 and 1:4.

In certain embodiments, the disclosed composition can optionally include pharmaceutically acceptable Vitamin C in the range of from 5 mg to 1000 mg.

In certain aspects, the total amount of Vitamin C present in the composition is about 5 mg.

In certain aspects, Vitamin C is not included in the microparticles of the nutritional composition. In other aspects, a portion of Vitamin C is included in any of the coated layers of the microparticles and another portion of Vitamin C is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of Vitamin C is not in the microparticles, and in this aspect, the remainder of Vitamin C can be included in the microparticle.

Vitamin C or ascorbic acid or ascorbate may be provided as an antioxidant to the patient or it may be provided as a stabilizer to prevent oxidation of the nutrients of the composition.

In certain embodiments, the disclosed nutritional composition can optionally include pharmaceutically acceptable Vitamin E in the range of from 10 IU to 1000 IU.

In certain aspects, the total amount of Vitamin E present in the nutritional composition is about 10 IU.

In certain aspects, Vitamin E is not included in the microparticles of the nutritional composition. In other aspects, a portion of Vitamin E is included in any of the coated layers of the microparticles and another portion of Vitamin E is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of Vitamin E is not in the microparticles, and in this aspect, the remainder of Vitamin E can be included in the microparticle.

In addition, any standard pharmaceutically acceptable excipient can be used in the nutritional composition. For example, these excipients can include diluents (e.g., mannitol, sorbitol, lactose, sucrose, and compressible sugars such as DiPac™ (dextrinized sucrose), available from Austin Products Inc., Holmdel, N.J.), splitting or swelling agents (e.g., polyvinyl polypyrrolidone, croscarmellose sodium (e.g., Ac-Di-Sol™ available from FMC BioPolymer, Philadelphia, Pa.), starches and derivatives, cellulose and derivatives, microcrystalline celluloses, such as Avicel™ PH 101 or Avicel™ CE-15 (a microcrystalline modified with guar gum), both available from FMC BioPolymer, Philadelphia, Pa.), lubricating agents (e.g., magnesium stearate), and flow agents (e.g., colloidal silicon dioxide, such as Cab-O-Sil M5 available from Cabot Corporation, Kokomo, Ind.).

In some aspects the magnesium folate-vitamin D composition may be blended with an antioxidant or other stabilizer for preservation; however, in another aspect, the magnesium folate-vitamin D composition is not mixed with additional excipients but is simply added to a composition. If the magnesium folate-vitamin D composition is not mixed with antioxidants, stabilizers, or excipients, refrigerating the magnesium folate-vitamin D composition will improve stability and shelf life.

Also, sweeteners can be included in the composition described herein. For example, sweeteners can be used to impart a pleasant flavor to the composition. Suitable sweeteners for use in the present disclosure include natural sweeteners such as sucrose, dextrose, fructose, invert sugar, mannitol, sorbitol, and the like, as well as synthetic sweeteners such as saccharin, aspartame, acesulfame potassium, cyclamates, and other commercial artificial sweeteners well-known to those of skill in the art. A preferred sweetener is acesulfame K (Sunett™ available from Nutrinova, Frankfort, Germany). The sweetener is added in an amount to achieve a desired sweetness. Typically, the sweetener is present in an amount from about 1.0 wt % to about 5.0 wt % of the overall weight of the nutritional composition. Flavors include vanilla and dulce de leche or caramel. Other flavors as chocolate or strawberry are also workable. Those skilled in the part will appreciate that the amount of sweetener may vary depending on the strength of the particular sweetener used and the levels approved by the regulatory authorities for use in pharmaceutical products.

Time Release Coatings

In certain aspects, the outermost surface of the encapsulating body and the outermost surface of the microparticle can independently include a time release coating. For example, in certain aspects the outermost surface of the encapsulating body can include a time release coating while such a coating is omitted from the microparticle. In other aspects, the outermost surface of the microparticle can include a time release coating while such a coating is omitted from the outermost surface of the encapsulating body.

Examples of these time release agents can include but are not limited to hydroxypropyl cellulose, hydroxypropyl methyl cellulose, hydroxypropyl methyl cellulose phthalate, pullulan, gelatin, collagen, casein, agar, gum arabic, dextrin, ethyl cellulose, methyl cellulose, chitin, chitosan, mannan, carboxymethylethyl cellulose, sodium carboxymethyl cellulose, polyethylene glycol, sodium alginate, poly(vinyl alcohol), cellulose acetate, poly(vinylpyrrolidone), silicone, poly (vinyl acetal) diethylamino acetate, albumin, adenine, cystine, D-tyrosine, or any combination thereof.

In certain aspects, these time release coatings may range from 1-15% of the overall weight of the composition.

EXAMPLES

Example 1

Microparticles Coated with Vitamin D and Magnesium

Microparticle cores can be prepared by extrusion spheronizer technology, and the microparticle cores can be subsequently made of magnesium, folate, and/or vitamin D, cellulose, starch, lactose, mannitol. Vitamin D and/or magnesium may comprise 25% to 50% of the microparticle core.

A pharmaceutically acceptable source of Vitamin D and/or magnesium may be mixed with a pharmaceutically acceptable neutral material such as tartaric acid, sugar sphere, calcium carbonate, mannitol, microcrystalline cellulose, silica, or starch which is then subjected to an extruding step to obtain microparticle cores in which 95% of the microparticle cores have an average particle diameter ranging from 90 µm to 500 um. These materials are mixed for 15-25 minutes and then extruded out an extruder.

Next, the microparticle cores are placed into a spheroidizer at 500 rpm for 5 to 10 seconds to ensure that sufficient microparticle core roundness is obtained.

After ensuring proper microparticle core roundness has been obtained, the microparticle cores are organized into a bed of microparticle cores that are subjected to a coating step. Next, the microparticle cores may also be (i) directly coated with an enteric coating to provide a dissolution rate profile and/or (ii) directly coated with a protective coating: solution, suspension, or dispersion or. The enteric coating may be L30D on different polymers. The enteric coating may comprise 1-5% of the weight of the total microparticle composition. The protective coating maybe hpmc. The protective coating may comprise 1-10% of the weight of the total microparticle composition.

Example 2

Exemplary Composition Formulations

Table 1 lists exemplary formulations of the composition of the present disclosure. The list is exemplary only and this disclosure is not limited to the examples below.

TABLE 1

| Ingredient | Exemplary Formulation 1 (wt %) | Exemplary Formulation 2 (wt %) | Exemplary Formulation 3 (wt %) |
| --- | --- | --- | --- |
| Vitamin $D_3$ | 3775 mg | 3775 mg | 3775 mg |
| Magnesium L-5-Methyltetrahydrofolate | 1 mg | 1 mg | 1 mg |
| NAC: Magnesium | 0 mg | 75 mg | 75 mg |
| Iron | 0 mg | 0 mg | 36 mg |
| From Heme | | | 6 mg (iron) |
| From Polysaccharide | | | 21 mg (iron) |
| From Chelate | | | 9 mg (iron) |

The formulations above do not include excipients, binders, stabilizers, etc. Glutathione and ascorbic acid may be used as stabilizers for folates. Tocopherols may be used as stabilizers or preservatives for Vitamin D.

As stated above, some of these compounds and nutrients will degrade or oxidize over time. Oftentimes commercial embodiments of nutritional compounds will require an "overage" to ensure that the composition will provide the intended amount of nutrient for a specific shelf life. The overages used in these commercial embodiments are considered equivalent to the embodiments of the present disclosure.

The foregoing description provides embodiments of the disclosure by way of example only. It is envisioned that other embodiments may perform similar functions and/or achieve similar results. Any and all such equivalent embodiments and examples are within the scope of the present disclosure and are intended to be covered by the appended claims.

It should be emphasized that the embodiments described herein are merely possible examples of implementations, merely set forth for a clear understanding of the principles of the present disclosure. Many variations and modifications may be made to the described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

One should note that conditional language, such as, among others, "can," "could," "might," or "may," unless specifically stated otherwise, or otherwise understood within the context as used, is generally intended to convey that certain embodiments include, while alternative embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment. Unless stated otherwise, it should not be assumed that multiple features, embodiments, solutions, or elements address the same or related problems or needs.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

What is claimed is:

1. A composition for human consumption comprising:
    folate, wherein the folate is levomefolate magnesium, in an amount of 1 mg,
    vitamin D in an amount ranging from 1800 IU to 1900 IU, and
    magnesium, wherein the magnesium is provided in the form of a magnesium chelate and magnesium salt selected from magnesium citrate, magnesium sulfate, magnesium oxide, magnesium chloride, magnesium acetate, magnesium hydroxide, magnesium gluconate, magnesium fumarate, or magnesium lactate.

2. The composition for human consumption of claim 1, wherein the magnesium chelate is an N-acetyl-L-cysteine ligand chelated with magnesium.

3. The composition for human consumption of claim 1, additionally comprising a source of iron, wherein the total amount of iron is between 5 mg and 90 mg.

4. The composition for human consumption of claim 1, wherein the Vitamin D is cholecalciferol.

5. The composition for human consumption of claim 1, wherein the composition is a softgel.

6. The composition for human consumption of claim 1, the total amount of magnesium is in an amount ranging from 25 mg and 100 mg.

7. The composition for human consumption of claim 6, wherein the composition is a softgel.

8. The composition for human consumption of claim 1, the magnesium salt is magnesium citrate.

9. The composition for human consumption of claim 8, wherein the magnesium citrate is in the amount of 250 mg.

10. A method of supplementing a folate deficiency for a human, the method comprising administrating the composition of claim 1.

11. The method of claim 10, wherein the Vitamin D is cholecalciferol.

12. The method of claim 10, wherein the magnesium chelate is an N-acetyl-L-cysteine ligand chelated with magnesium.

13. A composition for human consumption consisting essentially of:
  levomefolate magnesium in an amount of 1 mg,
  vitamin D in an amount ranging from 1800 IU to 1900 IU, and magnesium, and
  pharmaceutical excipients, wherein the magnesium is in the form of a magnesium chelate and magnesium citrate.

\* \* \* \* \*